United States Patent
Kawakami et al.

(10) Patent No.: US 9,556,089 B2
(45) Date of Patent: Jan. 31, 2017

(54) PURIFICATION METHOD AND PURIFICATION SYSTEM FOR PROPANE

(71) Applicant: SUMITOMO SEIKA CHEMICALS CO., LTD., Kako-gun, Hyogo (JP)

(72) Inventors: Junichi Kawakami, Kako-gun (JP); Shinichi Tai, Kako-gun (JP); Saori Tanaka, Kako-gun (JP)

(73) Assignee: SUMITOMO SEIKA CHEMICALS CO., LTD., Hyogo (JP)

(*) Notice: Subject to any disclaimer, the term of this patent is extended or adjusted under 35 U.S.C. 154(b) by 253 days.

(21) Appl. No.: 14/362,880

(22) PCT Filed: Oct. 3, 2012

(86) PCT No.: PCT/JP2012/075646
§ 371 (c)(1),
(2) Date: Jun. 4, 2014

(87) PCT Pub. No.: WO2013/094281
PCT Pub. Date: Jun. 27, 2013

(65) Prior Publication Data
US 2014/0343341 A1 Nov. 20, 2014

(30) Foreign Application Priority Data
Dec. 20, 2011 (JP) .................................. 2011-278031

(51) Int. Cl.
C07C 7/09 (2006.01)
C07C 7/12 (2006.01)
C07C 7/13 (2006.01)

(52) U.S. Cl.
CPC . *C07C 7/12* (2013.01); *C07C 7/09* (2013.01); *C07C 7/13* (2013.01)

(58) Field of Classification Search
CPC ............... C07C 7/09; C07C 7/12; C07C 7/11; B01D 53/02; B01D 53/14; B01D 53/1406; B01D 53/1487
USPC .................................................... 585/800 S
See application file for complete search history.

(56) References Cited

U.S. PATENT DOCUMENTS

| | | | | |
|---|---|---|---|---|
| 2,519,343 A | * | 8/1950 | Berg ...................... | B01D 53/08 95/111 |
| 3,306,006 A | * | 2/1967 | Urban ................ | B01D 53/0407 95/122 |
| 4,935,580 A | | 6/1990 | Chao et al. | |
| 2007/0261995 A1 | | 11/2007 | Canos et al. | |

FOREIGN PATENT DOCUMENTS

| | | |
|---|---|---|
| EP | 0 453 669 A1 | 10/1991 |
| EP | 1 825 901 A1 | 8/2007 |
| GB | 1375900 | 11/1974 |
| JP | 2008-513194 A | 5/2008 |
| WO | 2009/110492 A1 | 9/2009 |

OTHER PUBLICATIONS

Do et al., "Surface Diffusion and Adsorption of Hydrocarbons in Activated Carbon", AIChE Journal, vol. 47, No. 11, Nov. 2001, pp. 2515-2525.
Herden et al., "Adsorption of Hydrocarbons on Activated Carbons", Journal of Colloid and Interface Science, vol. 114, No. 2, Jul. 1991, pp. 477-482.
Habgood et al., "A Gas Chromatorgraphic Study of the Adsorptive Properties of a Series of Activated Charcoals" Canadian Journal of Chemistry, vol. 37, 1959, pp. 843-855.
Wang et al., "Multicomponent adsorption, desorption and displacement kinetics of hydrocarbons on activated carbon-dual diffusion and finite kinetics model", Separation and Purification Technology, 17, 1999, pp. 131-146.
International Search Report dated Dec. 18, 2012 issued in corresponding application No. PCT/JP2012/075646.
English Translation of Reply dated Dec. 18, 2012, filed in PCT/JP2012/075646.

* cited by examiner

*Primary Examiner* — Sharon Pregler
(74) *Attorney, Agent, or Firm* — Westerman, Hattori, Daniels & Adrian, LLP

(57) ABSTRACT

[PROBLEM] To provide an industrially advantageous method and system that are simple and have superior energy efficiency for obtaining high-purity propane from low-purity propane.

[SOLUTION] Water, carbon dioxide, at least one of ethane and propylene, and at least one of isobutane and normal butane present in low-purity propane in a gaseous phase are adsorbed by means of a zeolite molecular sieve that preferentially adsorbs water and carbon dioxide over propane, an activated carbon molecular sieve that preferentially adsorbs ethane and propylene over propane, and activated carbon that preferentially adsorbs isobutane and normal butane over propane. Propane is condensed in a state in which nitrogen and oxygen are maintained in a gaseous state by introducing the low-purity propane in a gaseous phase into a partial condenser. Nitrogen and oxygen in the gaseous phase are extracted from the partial condenser.

10 Claims, 2 Drawing Sheets

PURIFICATION METHOD AND PURIFICATION SYSTEM FOR PROPANE

TECHNICAL FIELD

The present invention relates to purification method and purification system for low-purity propane containing at least one of ethane and propylene, at least one of isobutane and normal butane, water, nitrogen, oxygen, and carbon dioxide as impurities, suitable for highly purifying the low-purity propane so as to have purity of, for example, 99.99% by volume or higher.

BACKGROUND ART

Propane used in liquefied petroleum gas (LPG), thermal power generation fuel, etc. is commonly purified industrially by fractional distillation of the petroleum as raw material. Consequently, propane currently in common use contains at least one of ethane and propylene, at least one of isobutane and normal butane, water, nitrogen, oxygen, and carbon dioxide as impurities, and the purity thereof is low and varies at a level on the order of 98.5% by volume.

However, the need for high-purity propane having a low concentration of impurities has increased in recent years. For example, there is a growing demand for propane as a raw material of high-withstand voltage silicon carbide (SiC) semiconductors. In order to realize this high level of withstand voltage performance of silicon carbide, the concentration of each impurity present in propane is required to be less than 1 ppm by volume, and in particular the concentration of nitrogen is required to be less than 0.1 ppm by volume.

Therefore, it is considered to distill high-purity propane from low-purity propane that is currently in common use having a purity of about 98.5% by volume. However, in the case of distilling high-purity propane from low-purity propane, the scale of the equipment becomes large and a large amount of energy is required. In the case of containing propylene in particular as an impurity, since the difference in boiling points between propane and propylene is small, the purification by distillation becomes difficult. Furthermore, a method of selectively absorbing propylene by an aqueous solution containing silver nitrate is known in order to separate propylene that is a member of olefins from propane that is a member of paraffins (see Patent Document 1). In this method, however, since propane, ethane, isobutane, and normal butane that are members of paraffins cannot be separated from each other, purification to high-purity propane cannot be achieved even if this method is employed.

PRIOR ART DOCUMENTS

Patent Documents

Patent Document 1: WO 2009/110492

SUMMARY OF THE INVENTION

Problem to be Solved by the Invention

According to the conventional purification technology, ethane, propylene, isobutane, normal butane, water, nitrogen, oxygen, and carbon dioxide that are impurities contained in low-purity propane cannot be reduced to trace amounts unless rectifying technology is used. Consequently, there are problems that the scale of equipment becomes large and energy costs are increased to obtain high-purity propane. An object of the present invention is to provide purification method and purification system for propane capable of solving such problems of the prior art.

Means of Solving the Problem

The inventors of the present invention focused on the respective properties of propane, ethane, propylene, isobutane, normal butane, nitrogen, oxygen, water, and carbon dioxide constituting low-purity propane, and found that the low-purity propane can be highly purified with separating the impurities by combining an adsorbing operation using a zeolite molecular sieve, an activated carbon molecular sieve, and an activated carbon with a partial condensing operation using a partial condenser, whereby the present invention is completed.

To be more precise, the method according the present invention is a purification method for low-purity propane containing at least one of ethane and propylene, at least one of isobutane and normal butane, water, nitrogen, oxygen, and carbon dioxide as impurities, the purification method for propane is characterized by comprising: an adsorption step of adsorbing water and carbon dioxide present in the low-purity propane in a gaseous phase by means of a zeolite molecular sieve that preferentially adsorbs water and carbon dioxide over propane; an adsorption step of adsorbing at least one of ethane and propylene present in the low-purity propane in a gaseous phase by means of an activated carbon molecular sieve that preferentially adsorbs ethane and propylene over propane; an adsorption step of adsorbing at least one of isobutane and normal butane present in the low-purity propane in a gaseous phase by means of activated carbon that preferentially adsorbs isobutane and normal butane over propane; a partial condensation step of condensing propane in a state in which nitrogen and oxygen are maintained in a gaseous phase by introducing the low-purity propane in a gaseous phase into a partial condenser; and an exhaust step of extracting nitrogen and oxygen in a gaseous phase from the partial condenser separately from the condensed propane, wherein the impurities are separated from the low-purity propane by the respective adsorption steps, the partial condensation step, and the exhaust step.

The present invention is based on the following findings.

If the effective pore diameter of the pores of a molecular sieve is set to a value that allows molecules of isobutane and normal butane to enter the pores, the impurities cannot be separated from propane with a molecular sieve alone because propane molecules also enter the pores. On the other hand, since ethane, propylene, water, and carbon dioxide are less easily adsorbed by activated carbon in comparison with isobutane and normal butane, if impurities are adsorbed by using only activated carbon that does not function as a molecular sieve, isobutane and normal butane are preferentially adsorbed by the adsorbent while adsorption of ethane, propylene, water, and carbon dioxide is inhibited. Consequently, the impurities cannot be separated from propane using activated carbon alone. Since ethane particularly has smaller molecular weight and weaker adsorptive power to activated carbon in comparison with isobutane and normal butane, it is difficult to separate ethane from propane with activated carbon alone. Moreover, since the adsorptive power of nitrogen and oxygen to an adsorbent is extremely low in comparison with other impurities, it is difficult to adsorb them with a molecular sieve or activated carbon.

According to the method of the present invention, ethane, propylene, water, and carbon dioxide which are less easily adsorbed by activated carbon in comparison with isobutane and normal butane can be separated from propane by a zeolite molecular sieve and activated carbon molecular sieve. Here, a hydrophilic zeolite molecular sieve having strong affinity with polar molecules is able to effectively adsorb carbon dioxide and water. In addition, a hydrophobic activated carbon molecular sieve performing high speed adsorption of ethane and propylene is able to effectively adsorb ethane and propylene. In addition, since isobutane and normal butane have greater molecular weights and larger Van der Waals force resulting in strong adsorptive power to activated carbon in comparison with propane, isobutane and normal butane can be separated from propane with activated carbon. Moreover, since the degrees of solubility of nitrogen and oxygen to propane are extremely low, they can be separated from propane by partial condensation. As a result, low-purity propane can be highly purified by separating the impurities.

There are no particular limitations on the order of the respective adsorption steps in the present invention. It is preferable that adsorbing with an activated carbon molecular sieve after adsorbing with a zeolite molecular sieve is followed by adsorbing with an activated carbon to improve propane collection rate. The partial condensation step can be carried out before or after all of the adsorption steps or can be carried out between any of the adsorption steps. By carrying out the partial condensation step after all of the adsorption steps, high-purity propane can be collected in the liquid phase without vaporizing the propane condensed in the partial condenser.

According to the method of the present invention, it is preferable that the low-purity propane is purified to a purity of 99.995% or higher to use the resulting high-purity propane as a raw material of a silicon carbide semiconductor, and purifying to a purity of 99.999% or higher is more preferable. According to the method of the present invention, such purification can be carried out easily.

The system of the present invention is a purification system for low-purity propane containing at least one of ethane and propylene, at least one of isobutane and normal butane, water, nitrogen, oxygen, and carbon dioxide as impurities, the purification system for propane is characterized by comprising: a first adsorption unit filled with a zeolite molecular sieve that preferentially adsorbs water and carbon dioxide over propane; a second adsorption unit filled with an activated carbon molecular sieve that preferentially adsorbs ethane and propylene over propane; a third adsorption unit filled with activated carbon that preferentially adsorbs isobutane and normal butane over propane; and a partial condenser, wherein the first adsorption unit, the second adsorption unit, the third adsorption unit, and the partial condenser are connected in series so as to form a propane flow path, a low-purity propane supply source is connected to one end of the propane flow path, a collection container for purified propane is connected to the other end of the propane flow path, a pressure regulating means that regulates pressure in the propane flow path is provided so that the low-purity propane in a gaseous phase is introduced into the first adsorption unit, the second adsorption unit, the third adsorption unit, and the partial condenser, the partial condenser has a cooling means for the low-purity propane so that propane is condensed in the partial condenser in a state in which nitrogen and oxygen are maintained in a gaseous phase, and an exhaust path is provided for extracting nitrogen and oxygen in a gaseous phase from the partial condenser.

According to the system of the present invention, the pressure in the propane flow path is regulated so that the low-purity propane in a gaseous state is introduced into each of the adsorption units and the partial condenser. As a result, the low-purity propane in a gaseous phase is introduced into the respective adsorption units and the partial condenser via one end of the propane flow path. In respective adsorption units, at a pressure that exceeds atmospheric pressure, water and carbon dioxide can be adsorbed by the activated carbon molecular sieve, at least one of ethane and propylene can be adsorbed by the activated carbon molecular sieve, and at least one of isobutane and normal butane can be adsorbed by the activated carbon. The low-purity propane introduced into the partial condenser is cooled, and propane is condensed in a state in which nitrogen and oxygen are maintained in a gaseous phase. Nitrogen and oxygen in a gaseous phase are extracted via the exhaust path separately from the condensed propane in the partial condenser. The highly purified propane that flows out from the other end of the propane flow path is collected in the collection container.

The method of the present invention can be carried out by the system of the present invention.

It is preferable that the zeolite molecular sieve is of type 4A. Moreover, it is preferable that the activated carbon molecular sieve is of type 4A. As a result, commonly used molecular sieves can be adopted.

In the system of the present invention, it is preferable that the propane flow path has a plurality of branched flow paths mutually connected in parallel, the first adsorption unit, the second adsorption unit, and the third adsorption unit are connected in series in each of the branched flow paths, temperature control means that regulates internal temperature in the first adsorption unit, the second adsorption unit, and the third adsorption unit is provided, a first connection switching mechanism that is capable of switching one end of each of the branched flow paths between a state of being connected to the low-purity propane supply source and a state of being connected to an atmospheric pressure region is provided, and a second connection switching mechanism that is capable of switching the other end of each of the branched flow paths between a state of being connected to the collection container, a state of being connected to a regeneration gas supply source, and a closed state is provided.

As a result of employing this configuration, while the adsorption of impurities is carried out by the adsorption units in any of the branched flow paths, regeneration of the zeolite molecular sieve, the activated carbon molecular sieve, and the activated carbon which are adsorbent in the adsorption units in the remain of the branched flow paths can be carried out.

To be more precise, when impurities are adsorbed by adsorption units in any of the branched flow paths, one end of the branched flow path is connected to the low-purity propane supply source, and the other end is connected to the collection container. When the adsorbent in the adsorption units in any of the branched flow paths is regenerated, one end of the branched flow paths is connected to the atmospheric pressure region, and the other end is closed, whereby gas remaining inside the adsorption units is exhausted to the atmospheric pressure region. The internal temperature of the adsorption units is then raised and impurities are desorbed from the adsorbent. In addition, the regeneration gas is flowed towards one end of the branched flow path in a state in which the other end of the branched flow paths is connected to the regeneration gas supply source, whereby the desorbed impurities are exhausted to the atmospheric pressure region. As a result, adsorption of impurities can be carried out continuously.

In the system of the present invention, it is preferable that a compressor that has an intake port connected to the other end of each of the branched flow paths is provided, a temporary storage container that is connected to the outlet of the compressor is provided, the first switching mechanism is capable of switching one end of each of the branched flow paths between a closed state and a state of being connected to the temporary storage container, and the second switching mechanism is capable of switching the other end of each of the branched flow paths between a state of being connected to the intake port of the compressor and a state of being connected to an atmospheric pressure region.

As a result of employing this configuration, propane remaining in the adsorption units can be collected after the adsorption steps and before the regeneration is carried out. The collected propane can be used to exhaust the regeneration gas remaining in the adsorption units at the beginning of the restart of the adsorption steps.

To be more precise, after the adsorption steps in the adsorption units in the branched flow path is completed, one end of the branched flow path is closed and the other end is connected to the partial condenser. As a result, propane remaining in the adsorption units can be aspirated and stored in the temporary storage container. Subsequently, after regenerating the adsorbent in the adsorption unit and before beginning the adsorption steps, one end of the branched flow path is connected to the temporary storage container while the other end is connected to the atmospheric pressure region. As a result, the regeneration gas remaining in the adsorption units can be exhausted to the atmospheric pressure region by the flow of propane stored in the temporary storage container. Subsequently, one end of the branched flow path is connected to the low-purity propane supply source and the other end is connected to the collection container, thereby making it possible to carry out the purification of the low-purity propane.

Effect of the Invention

According to the present invention, industrially advantageous method and system that are simple and have superior energy efficiency can be provided for obtaining high-purity propane from low-purity propane, the resulting high-purity propane can be used as a raw material of, for example, silicon carbide semiconductors.

MODES FOR CARRYING OUT THE INVENTION

Figure 1:
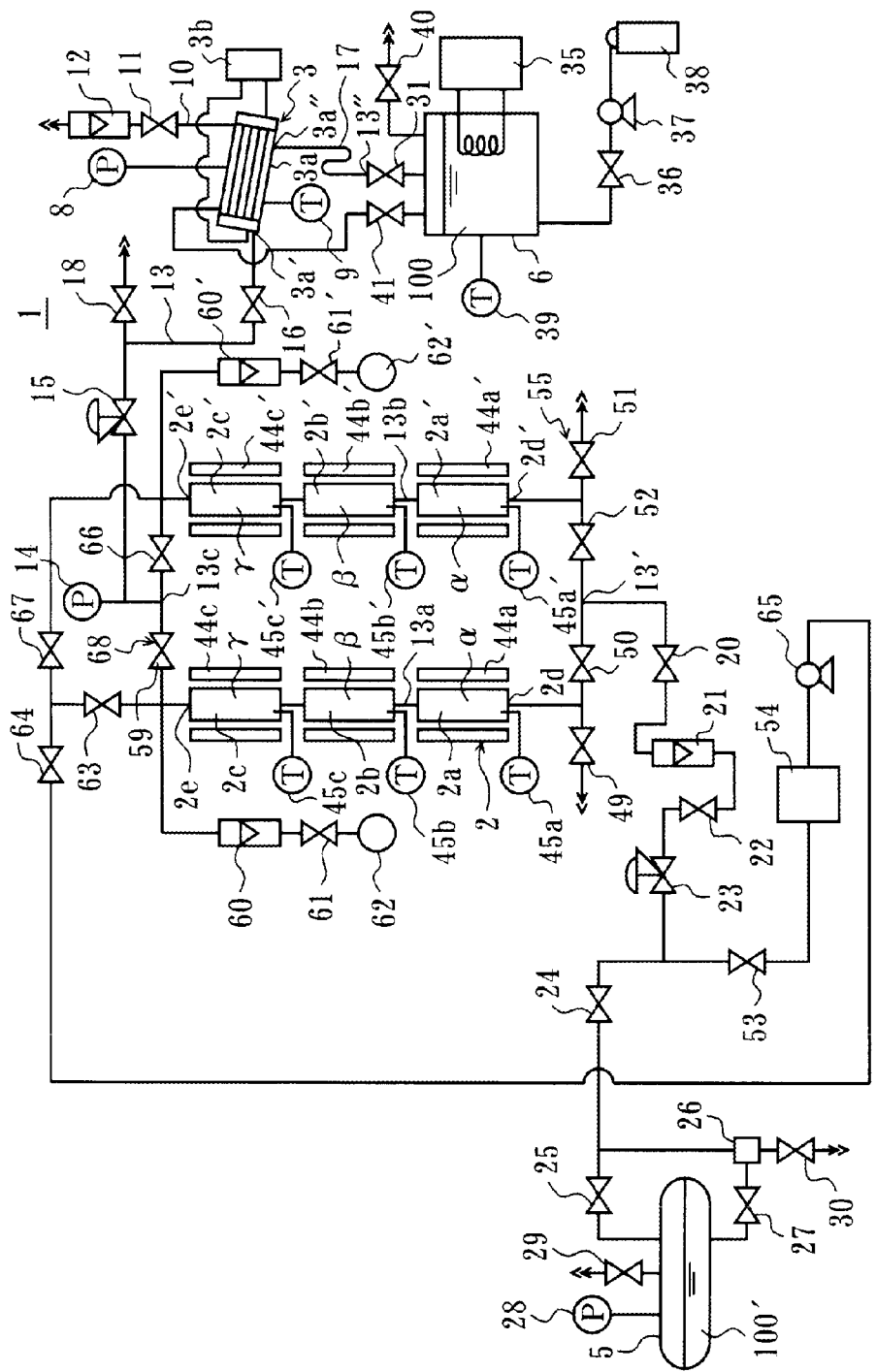
FIG. 1 Drawing explaining the configuration of a propane purification system according to a first embodiment of the present invention.

A propane purification system 1 of a first embodiment shown in FIG. 1 is provided with an adsorber 2 and a partial condenser 3, and is used to highly purify low-purity propane 100' supplied from a supply source 5 and collect high-purity propane 100 in a collection container 6.

The low-purity propane 100' to be purified by the purification system 1 contains ethane, propylene, isobutane, normal butane, water, nitrogen, oxygen, and carbon dioxide as impurities. Although there are no particular limitations on the purity of the low-purity propane 100', it is preferably 95% by volume through 99% by volume, and low-purity propane having a purity of 98.5% by volume or less that is commonly purified industrially by fractional distillation of petroleum can be used. The purity of the high-purity propane 100 obtained by the present purification system 1 is normally 99.99% by volume or higher, and can be made to 99.995% by volume or higher, and can further be made to 99.999% by volume or higher. Therefore, high-purity propane suitable for use as a raw material of silicon carbide semiconductors can be easily obtained.

The adsorber 2 has two first adsorption towers 2a and 2a' as first adsorption unit, two second adsorption towers 2b and 2b' as second adsorption unit, and two third adsorption towers 2c and 2c' as third adsorption unit. The first adsorption towers 2a and 2a are filled with a zeolite molecular sieve α that preferentially adsorbs water and carbon dioxide over propane. The second adsorption towers 2b and 2b' are filled with an activated carbon molecular sieve β that preferentially adsorbs ethane and propylene over propane. The third adsorption towers 2c and 2c' are filled with an activated carbon γ that preferentially adsorbs isobutane and normal butane over propane.

The effective pore diameter of the pores of the zeolite molecular sieve α filled in the first adsorption towers 2a and 2a' is set to a value that allows water molecules and carbon dioxide molecules to enter the pores while does not allow propane molecules to enter the pores.

The effective pore diameter of the pores of the activated carbon molecular sieve β filled in the second adsorption towers 2b and 2b' is set to a value that allows ethane molecules and propylene molecules to enter the pores while does not allows propane molecules to enter the pores.

The zeolite molecular sieve α and the activated carbon molecular sieve β of the present embodiment are each of type 4A. As a result, the effective diameter of the pores of each of the zeolite molecular sieve α and the activated carbon molecular sieve β is 0.4 nm (4 Å). The zeolite molecular sieve α is hydrophilic and has strong affinity for polar molecules, while the activated carbon molecular sieve β is hydrophobic and performs high speed adsorption of ethane and propylene. As a result, water and carbon dioxide can be preferentially effectively adsorbed over propane by the zeolite molecular sieve α, and ethane and propylene can be preferentially effectively adsorbed over propane by the activated carbon molecular sieve β. In addition, there are no particular limitations on the form of the zeolite molecular sieve α and the activated carbon molecular sieve β, for example, they can be in the form of granules or pellets.

If the effective diameter of the pores of the zeolite molecular sieve α is 0.3 nm, carbon dioxide molecules are unable to enter, while if it is 0.5 nm, even isobutane molecules and normal butane molecules are able to enter. If the effective pore diameter of the pores of the activated carbon molecular sieve β is 0.3 nm, ethane molecules are unable to enter, while if it is 0.5 nm, even isobutane molecules and normal butane molecules are able to enter. Therefore, in the case of using molecular sieves as the zeolite molecular sieve α and activated carbon molecular sieve β other than type 4A, each effective pore diameter of the pores is preferably set to a unified value between 0.3 nm and 0.5 nm so that they are able to perform the function of molecular sieves for screening molecules based on the molecular size. As a result, water and carbon dioxide are able to enter the pores of the zeolite molecular sieve α preferentially over propane, ethane molecules and propylene molecules are able to enter the pores of the activated carbon molecular sieve β preferentially over propane molecules, and isobutane molecules and normal butane molecules can be prevented to enter therein. In addition, in the case one of ethane and propylene is contained as impurity in the low-purity propane 100', the effective pore diameter of the pores of the activated carbon molecular sieve β can be set to a unified value that allows the contained molecules to enter while does not allow propane molecules to enter, and a type 4A activated carbon molecular sieve β can be used if it is set to a value of 0.4 nm.

The necessary and sufficient property of the activated carbon γ filled in the third adsorption towers 2c and 2c' is to preferentially adsorb isobutane and normal butane over propane. It is preferable that the activated carbon γ does not function as a molecular sieve in which the pore diameter is not unified, and has an average effective pore diameter of 0.5 nm or more.

The ordinary activated carbon that does not function as a molecular sieve allows molecules of isobutane and normal butane to enter the pores, the average effective pore diameter of which is 0.5 nm or more. Furthermore, it is preferable that the activated carbon γ to be adopted is not adhered by chemicals such as acid, alkali, and the like in order to prevent the high-purity propane from being contaminated. For example, coconut shell activated carbon or coal-based activated carbon can be adopted. There are no particular limitations on the form of the activated carbon γ, for example, it can be in the form of granules or pellets. In addition, the pore diameter of the activated carbon γ can be unified provided it does not function as a molecular sieve for ethane, propylene, propane, isobutane, normal butane, water and carbon dioxide, in this case, the effective pore diameter of the pores is preferably 0.5 nm or more so as to allow isobutane and normal butane molecules to enter the pores.

An ordinary partial condenser used for industrial purposes can be adopted as the partial condenser 3, the necessary and sufficient capability of which is to condense propane in a state in which nitrogen and oxygen are maintained in a gaseous phase by cooling the low-purity propane 100' by a cooling means. The partial condenser 3 of the present embodiment has a shell-and-tube-type heat exchanger 3a, and a constant temperature fluid circulation device 3b that functions as the cooling means. A constant temperature fluid circulated by the constant temperature fluid circulation device 3b flows in the shell of the heat exchanger 3a and cools the low-purity propane 100' that is introduced into the tube of the heat exchanger 3a from a propane inlet 3a' of the partial condenser 3. The constant temperature fluid is composed of, for example, a mixed liquid of water and ethanol. The resultingly condensed propane flows towards a propane outlet 3a" of the partial condenser 3 by inclining the axial direction of the tube by, for example, 1 degree through 5 degrees to the horizontal direction. In addition, a pressure gauge 8 and a temperature gauge 9 are provided to measure the pressure and temperature of the region where propane is condensed in the partial condenser 3.

An exhaust path 10 is provided for extracting nitrogen and oxygen in a gaseous phase from the partial condenser 3. To be more precise, the exhaust path 10 branches from the flow path of propane in the partial condenser 3, and is connected to an atmospheric pressure region via an on-off valve 11 and a flow regulator 12. As a result, nitrogen and oxygen in a gaseous phase can be exhausted from the partial condenser 3 to an atmospheric pressure region.

The one first adsorption towers 2a, the one second adsorption towers 2b, and the one third adsorption towers 2c constitute a first branched flow path 13a by being connected in series with piping. In addition, the other first adsorption tower 2a', the other second adsorption tower 2b', and the other third adsorption tower 2c' constitute a second branched flow path 13b by being connected in series with piping. Both of the branched flow paths 13a and 13b are connected in parallel with piping, and are connected in series to the partial condenser 3 with piping. As a result, the first adsorption unit, the second adsorption unit, the third adsorption unit, and the partial condenser 3 are connected in series to constitute a propane flow path 13.

A connecting section between an inlet 2d of the one first adsorption towers 2a on one end of the first branched flow path 13a and an inlet 2d' of the other first adsorption tower 2a' on one end of the second branched flow path 13b constitutes one end 13' of the propane flow path 13.

A connecting section 13c between an outlet 2e of the one third adsorption towers 2c on the other end of the first branched flow path 13a and an outlet 2e' of the other third adsorption tower 2c' on the other end of the second branched flow path 13b is connected to the propane inlet 3a of the partial condenser 3 via a pressure gauge 14, a pressure regulating valve 15, and an on-off valve 16. A trap line 17 connected to the propane outlet 3a" of the partial condenser 3 has a leading end constituting the other end 13" of the propane flow path 13. Furthermore, the connecting section 13c is connected to an atmospheric pressure region via the pressure gauge 14, the pressure regulating valve 15, and an on-off valve 18.

The one end 13' of the propane flow path 13 is connected to the supply source 5 of the low-purity propane 100'. To be more precise, an on-off valve 20, a flow regulator 21, an on-off valve 22, a pressure regulating valve 23, and an on-off valve 24 are connected in series to the one end 13' of the propane flow path 13. The on-off valve 24 is connected to the upper space of a tank forming the supply source 5 via an on-off valve 25, and is connected to the lower space of that tank via a vaporizer 26 and an on-off valve 27. The flow path from the on-off valve 24 to the upper space of the supply source 5 and the flow path from the on-off valve 24 to the lower space of the supply source 5 are in parallel. The one end 13' of the propane flow path 13 can be selectly connected to the upper space or the lower space of the supply source 5 by switching of the on-off valves 25 and 27.

The supply source 5 of the present embodiment stores the low-purity propane 100' in a liquid phase. Accordingly, the low-purity propane 100' stored in the lower space of the supply source 5 can be vaporized after being flowed out through the on-off valve 27 in a liquid phase, or can be flowed out through the on-off valve 25 after being vaporized in the upper space of the supply source 5. In addition, a pressure gauge 28 for measuring internal pressure of the supply source 5 is connected, the upper space of the supply source 5 is connected to an atmospheric pressure region via an on-off valve 29, and a drain valve 30 is connected to the vaporizer 26. The on-off valve 29 is normally closed.

The other end 13" of the propane flow path 13 is connected to the collection container 6, which stores highly purified propane, via an on-off valve 31. The high-purity propane 100 in a liquid phase collected in the collection container 6 is cooled by a constant temperature fluid circulation device 35. The high-purity propane 100 is charged into a charging container 38 from the collection container 6 via an on-off valve 36 and a compressor 37. A temperature gauge 39 is provided for measuring the temperature of the collection container 6, and the high-purity propane 100 is cooled by the constant temperature fluid circulation device 35 in response to the temperature measured by the temperature gauge 39. The upper space of the collection container 6 is connected to an atmospheric pressure region via an on-off valve 40, and connected to the propane flow path in the partial condenser 3 via an on-off valve 41. The on-off valves 40 and 41 are normally closed.

The pressure regulating valve 23 regulates the pressure of the low-purity propane 100' introduced into the propane flow path 13 so as to be lower than the pressure in the supply source 5. The pressure regulating valve 15 regulates the back pressure of the adsorption towers 2a, 2a', 2b, 2b', 2c and 2c' that are adsorption units so as to be lower than the pressure of the low-purity propane 100' regulated by the pressure regulating valve 23. As a result, the pressure regulating valves 15 and 23 function as pressure regulating means that regulate the pressure in the propane flow path 13. As a result of regulating the pressure in the propane flow path 13, the low-purity propane in a gaseous phase can be introduced into the respective adsorption towers 2a, 2a', 2b, 2b', 2c and 2c' and the partial condenser 3.

Electric heaters 44a, 44b, 44c, 44a', 44b' and 44c' are provided as temperature regulating means that regulates the internal temperature in the respective adsorption towers 2a, 2a', 2b, 2b', 2c and 2c'. Temperature gauges 45a, 45b, 45c, 45a', 45b' and 45c' are provided for measuring the internal temperature in the respective adsorption towers 2a, 2a', 2b, 2b', 2c and 2c'.

The inlet 2d of the one first adsorption towers 2a, which is one end of the first branched flow path 13a, is connected to an atmospheric pressure region via an on-off valve 49, and connected to one end 13' of the propane flow path 13 via an on-off valve 50. The inlet 2d' of the other first adsorption tower 2a', which is one end of the second branched flow path 13b, is connected to an atmospheric pressure region via an on-off valve 51, and connected to the one end 13' of the propane flow path 13 via an on-off valve 52. The one end 13' of the propane flow path 13 is connected to the supply source 5 of the low-purity propane 100' as previously described, and connected to a temporary storage container 54 via an on-off valve 53 connected to the inlet of the pressure regulating valve 23. As a result, a first connection switching mechanism 55 that is capable of switching each of the one ends of the branched flow paths 13a and 13b between a state in which it is connected to the supply source 5 of the low-purity propane 100', a state in which it is connected to an atmospheric pressure region, a closed state, and a state in which it is connected to the temporary storage container 54 is provided.

The outlet 2e of the one third adsorption towers 2c, which is the other end of the first branched flow path 13a, is connected to the connecting section 13c via an on-off valve 59, connected to a regeneration gas supply source 62 via a flow regulator 60 and an on-off valve 61, and connected to the intake port of a compressor 65 via an on-off valve 63 and an on-off valve 64. The outlet of the compressor 65 is connected to the temporary storage container 54. The outlet 2e' of the other third adsorption tower 2c', which is the other end of the second branched flow path 13b, is connected to the connecting section 13c via an on-off valve 66, connected to a regeneration gas supply source 62' via a flow regulator 60' and an on-off valve 61', and connected to the intake port of the compressor 65 via an on-off valve 67 and the on-off valve 64. As previously described, the connecting section 13c is connected to the collection container 6 via the on-off valve 16 and connected to an atmospheric pressure region via the on-off valve 18. As a result, a second connection switching mechanism 68 that is capable of switching the respective other ends of the branched flow paths 13a and 13b between a state of being connected to the collection container 6, a state of being connected to the regeneration gas supply sources 62 and 62', a state of being connected to the intake port of the compressor 65, and a state of being connected to an atmospheric pressure region is composed.

The following provides a description of the procedure for purifying the low-purity propane 100' with the above-mentioned purification system 1. Here, although the purification procedure using the adsorption towers 2a, 2b and 2c that are adsorption units of the first branched flow path 13a is described, the purification procedure using the adsorption towers 2a', 2b' and 2c' that are adsorption units of the second branched flow path 13b is the same.

First, the pressure in the adsorption towers 2a, 2b and 2c are set to a prescribed value by introducing the low-purity propane therein, and regeneration gas used in the aftermentioned regeneration step is purged from the adsorption towers 2a, 2b and 2c by carrying out an initial adsorption step.

In the initial adsorption step, the on-off valve 50, the on-off valve 20, the on-off valve 22, and the on-off valve 53 are opened in order to connect one end of the first branched flow path 13a to the temporary storage container 54. Furthermore, the on-off valve 59 and the on-off valve 18 are opened in order to connect the other end of the first branched flow path 13a to an atmospheric pressure region. The on-off valve 16, the on-off valve 24, the on-off valve 49, the on-off valve 52, the on-off valve 61, the on-off valve 63, and the on-off valve 66 are closed. At this time, the flow rate of the low-purity propane 100' that flows out from the temporary storage container 54 is regulated by the flow regulator 21, and the pressure thereof is regulated by the pressure regulating valve 23. Furthermore, the pressure inside the adsorption towers 2a, 2b and 2c is regulated to an adsorption pressure by the pressure regulating valve 15, and the temperature inside the adsorption towers 2a, 2b and 2c is regulated to room temperature. The pressure of the low-purity propane is regulated by the pressure regulating valve 23 so as to be higher than the adsorption pressure set by the pressure regulating valve 15 in the adsorber 2. The adsorption pressure is regulated to a value that exceeds atmospheric pressure at which propane is prevented from liquefying under normal temperature in order to effectively utilize the adsorption capacity of the zeolite molecular sieve α, the activated carbon molecular sieve β, and the activated carbon γ that are adsorbents. The adsorption pressure is preferably regulated to, for example, a gauge pressure of about 0.5 MPa through 0.6 MPa. As a result, the regeneration gas inside the adsorption towers 2a, 2b and 2c is purged to an atmospheric pressure region by the low-purity propane 100' in a gaseous phase supplied from the temporary storage container 54, and the impurities present in the low-purity propane 100' are adsorbed by the adsorbents α, β and γ. As a result of this initial adsorption step, the insides of the adsorption towers 2a, 2b and 2c are preferably filled with the regeneration gas at a concentration of 100 ppm by volume or less and the low-purity propane 100' that takes all the rest. Since the regeneration gas present in the adsorption towers 2a, 2b and 2c is separated from the propane by means of the partial condenser 3 in the subsequent adsorption step, a step for separating the regeneration gas is not required.

In addition, at the start of operation of the system, the low-purity propane 100' is not stored in the temporary storage container 54 and the regeneration step is not carried out. In this instance, after filling the adsorption towers 2a, 2b and 2c with the regeneration gas preliminarily, the initial adsorption step can be carried out using the low-purity propane 100' supplied from the supply source 5 instead of the low-purity propane 100' in the temporary storage container 54 by opening the on-off valve 24, closing the on-off valve 53, and opening one of the on-off valve 25 and the on-off valve 27.

The adsorption step is carried out after the initial adsorption step. To be more precise, the on-off valve 50, the on-off valve 20, the on-off valve 22, the on-off valve 24, and one of the on-off valve 25 and the on-off valve 27 are opened in order to connect one end of the first branched flow path 13a to the supply source 5 of the low-purity propane 100'. Furthermore, the on-off valve 59, the on-off valve 16, and the on-off valve 31 are opened in order to connect the other end of the first branched flow path 13a to the collection container 6. The on-off valve 18, the other of the on-off valve 25 and the on-off valve 27, the on-off valve 49, the on-off valve 52, the on-off valve 53, the on-off valve 61, the on-off valve 63, and the on-off valve 66 are closed.

As a result, the low-purity propane 100' in a gaseous phase is introduced into the respective adsorption towers 2a, 2b and 2c of the first branched flow path 13a. The flow rate of the low-purity propane 100' is appropriately regulated by the flow regulator 21. In the first adsorption tower 2a, an adsorption step of adsorbing water and carbon dioxide in the low-purity propane in a gaseous phase by means of the zeolite molecular sieve α is carried out. In the second adsorption tower 2b, an adsorption step of adsorbing ethane and propylene in the low-purity propane in a gaseous phase by means of the activated carbon molecular sieve β is carried out. In the third adsorption tower 2c, an adsorption step of adsorbing isobutane and normal butane in the low-purity propane in a gaseous phase by means of the activated carbon γ is carried out. The adsorption pressure in each of the adsorption steps, the flow rate of the low-purity propane 100', and the temperatures in the adsorption towers 2a, 2b and 2c are regulated in the same manner as in the initial adsorption step.

The low-purity propane 100' in a gaseous phase is introduced into the partial condenser 3 after passing through the first branched flow path 13a. As a result, a partial condensation step of condensing the propane in a state in which nitrogen and oxygen are maintained in a gaseous phase is carried out in the partial condenser 3. At this time, the temperature measured by the temperature gauge 9 in the tubes of the partial condenser 3 is set by regulating the temperature of the constant temperature fluid circulated by the constant temperature fluid circulation device 3b of the partial condenser 3. This temperature setting can be carried out so that the pressure measured by the pressure gauge 8 becomes lower than the pressure measured by the pressure gauge 14 in the adsorption units and propane is condensed in a state in which nitrogen and oxygen in the low-purity propane 100' are maintained in a gaseous phase at that pressure.

Nitrogen and oxygen in a gaseous phase in the partial condenser 3 are exhausted from the exhaust path 10 to an atmospheric pressure region. As a result, an exhaust step of extracting nitrogen and oxygen in a gaseous phase from the partial condenser 3 separately from the condensed propane is carried out. The impurities are separated from the low-purity propane 100' by the above-mentioned respective adsorption steps, the above-mentioned partial condensation step, and the above-mentioned exhaust step. As a result, propane that is condensed in the partial condenser 3 is collected in the collection container 6 as a high-purity propane in a liquid phase. The exhaust flow rate from the exhaust path 10 regulated by the flow regulator 12 can be set so that the oxygen concentration and nitrogen concentration in the high-purity propane collected in the collection container 6 become desired values. For example, if the nitrogen concentration at the outlets of the third adsorption towers 2c and 2c' is 10 ppm, the nitrogen concentration of the high-purity propane in the collection container 6 can be made to be 1 ppm or less by setting the flow rate regulated by means of the flow regulator 12 to about 5% by volume through 10% by volume with respect to the flow rate regulated by means of the flow regulator 21. The adsorption steps end before the start of breakthrough of the adsorbents α, β and γ in the adsorption towers 2a, 2b and 2c due to lost of the required adsorption capability. The time until the start of breakthrough can be predetermined by experiment.

A temporary storage step is carried out after the adsorption steps. To be more precise, the on-off valve 50 is closed in order to close one end of the first branched flow path 13a, while the on-off valve 59 is closed and the on-off valve 63 and the on-off valve 64 are opened in order to connect the other end of the first branched flow path 13a to the intake port of the compressor 65. Subsequently, the low-purity propane 100' remaining in the adsorption towers 2a, 2b and 2c is aspirated by the compressor 65 and stored in the temporary storage container 54. Since the low-purity propane 100' stored in the temporary storage container 54 passes through the supply part, the purity thereof is higher than the purity of the low-purity propane 100' in the supply source 5. Accordingly, impurities to be adsorbed by the adsorbents α, β and γ in the initial adsorption step can be reduced. Aspiration of the low-purity propane 100' by the compressor 65 is carried out until, for example, the pressures in the adsorption towers 2a, 2b and 2c roughly reach atmospheric pressure.

The regeneration step is carried out after the temporary storage step. To be more precise, the on-off valve 50 and the on-off valve 59 are closed while the on-off valve 49 and the on-off valve 61 are opened in order to connect one end of the first branched flow path 13a to an atmospheric pressure region and connect the other end of the first branched flow path 13a to the regeneration gas supply source 62. In this state, the internal temperatures of the adsorption towers 2a, 2b and 2c are raised by the electric heaters 44a, 44b and 44c with confirming the temperature gauges 45a, 45b and 45c. Furthermore, the regeneration gas from the supply source 62 is introduced into the adsorption towers 2a, 2b and 2c through the other end of the first branched flow path 13a with regulating the flow rate by means of the flow regulator 60, and then exhausted from the one end of the first branched flow path 13a to an atmospheric pressure region. Due to the rising in temperature, impurities are desorbed from the adsorbents α, β and γ in the adsorption towers 2a, 2b and 2c, and the desorbed impurities are exhausted to an atmospheric pressure region together with the regeneration gas. As a result, the regeneration step is carried out in which the regeneration gas in the adsorption towers 2a, 2b and 2c is flowed in a direction opposite to the direction of flow of the low-purity propane 100' in the adsorption steps.

The temperature in the adsorber 2 in the regeneration step is preferably 200° C. through 300° C., and more preferably about 250° C. If the temperature is below 200° C., regeneration time becomes long, while if the temperature exceeds 300° C., energy costs increase and there is a risk of progression of powdering of the zeolite molecular sieve α, the activated carbon molecular sieve β, and the activated carbon γ. If the respective concentrations of impurities contained in the regeneration gas exhausted from one end of the first branched flow path 13a are made to be 50 ppm or less, the adsorption capacity of the zeolite molecular sieve α, the activated carbon molecule sieve β, and the activated carbon γ can be restored to 90% or more of the initial adsorption capacity. The regeneration time required to restore the adsorption capacity to this level can be experimentally determined since it varies according to the flow rate of the regeneration gas, the amount of adsorbed impurities, and the temperatures in the adsorption towers 2a, 2b and 2c. In addition, it is preferable that the gas used as the regeneration gas is inert gas such as helium, argon, or the like that is inert to propane, zeolite molecular sieve α, activated carbon molecular sieve β, activated carbon γ, and structural materials of the purification system 1, etc. that contact in the regeneration step. Above-mentioned initial adsorption step is restarted after completion of the regeneration step.

While the initial adsorption step and the adsorption step are carried out in one of the adsorption towers 2a, 2b, 2c of the first branched flow path 13a and the adsorption towers 2a', 2b', 2c' of the second branched flow path 13b, the temporary storage step and the regeneration step can be carried out in the other. As a result, the adsorption of impurities from the low-purity propane 100' can be carried out continuously.

Figure 2:
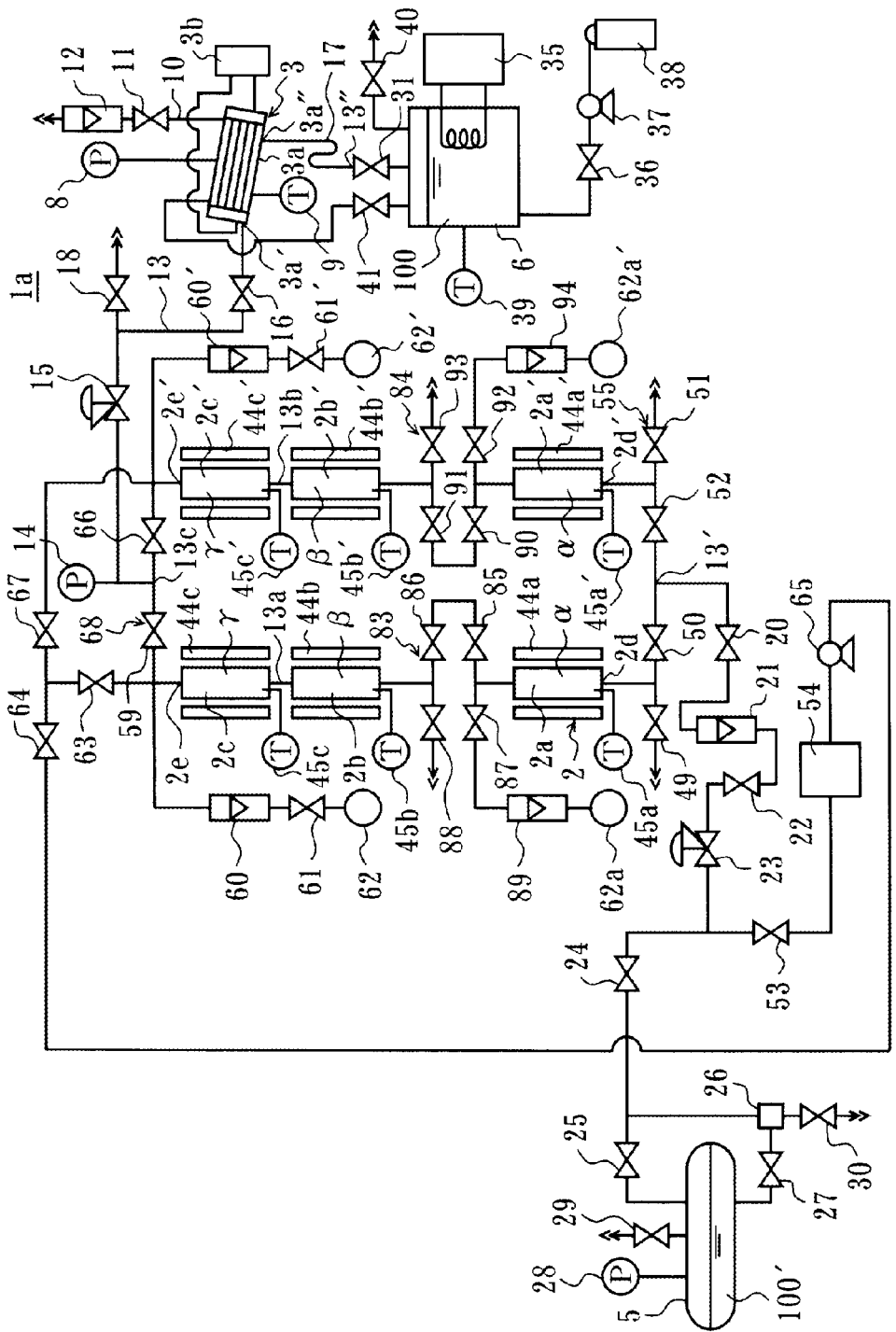
FIG. 2 Drawing explaining the configuration of a propane purification system according to a second embodiment of the present invention.

FIG. 2 indicates a propane purification system 1a according to a second embodiment, and those components that are the same as those of the first embodiment are indicated with the same reference symbols. A purification system 1a of the second embodiment comprises a third connection switching mechanism 83 provided between the first adsorption tower 2a and the second adsorption tower 2b in the first branched flow path 13a, and a fourth connection switching mechanism 84 provided between the first adsorption towers 2a' and the second adsorption tower 2b' in the second branched flow path 13b.

The third connection switching mechanism 83 has two on-off valves 85 and 86 provided in a flow path between the outlet of the first adsorption tower 2a and the inlet of the second adsorption tower 2b, an on-off valve 87 connected to an area between the outlet of the first adsorption tower 2a and the on-off valve 85, and an on-off valve 88 connected to an area between the inlet of the second adsorption tower 2b and the on-off valve 86. A regeneration gas supply source 62a is connected to the on-off valve 87 via a flow regulator 89. The on-off valve 88 is connected to an atmospheric pressure region. As a result, it is switched between a state in which the outlet of the first adsorption tower 2a is connected to the inlet of the second adsorption tower 2b by opening the on-off valves 85 and 86 and closing the on-off valves 87 and 88, a state in which the outlet of the first adsorption tower 2a is connected to the regeneration gas supply source 62a and the inlet of the second adsorption tower 2b is connected to an atmospheric pressure region by closing the on-off valves 85 and 86 and opening the on-off valves 87 and 88, and a state in which the outlet of the first adsorption tower 2a is connected to the inlet of the second adsorption tower 2b by closing the on-off valves 85, 86, 87 and 88.

The fourth connection switching mechanism 84 has two on-off valves 90 and 91 provided in a flow path between the outlet of the first adsorption tower 2a' and the inlet of the second adsorption tower 2b', an on-off valve 92 connected to an area between the outlet of the first adsorption tower 2a' and the on-off valve 90, and an on-off valve 93 connected to an area between the inlet of the second adsorption tower 2b' and the on-off valve 91. A regeneration gas supply source 62a is connected to the on-off valve 92 via a flow regulator 94. The on-off valve 93 is connected to an atmospheric pressure region. As a result, it is switched between a state in which the outlet of the first adsorption tower 2a is connected to the inlet of the second adsorption tower 2b' by opening the on-off valves 90 and 91 and closing the on-off valves 92 and 93, a state in which the outlet of the first adsorption tower 2a is connected to the regeneration gas supply source 62a' and the inlet 2b' of the second adsorption tower is connected to an atmospheric pressure region by closing the on-off valves 90 and 91 and opening the on-off valves 92 and 93, and a state in which the outlet of the first adsorption tower 2a is connected to the inlet of the second adsorption tower 2b' by closing the on-off valves 90, 91, 92 and 93. The remainder of the components are the same as those of the first embodiment.

In the temporary storage step of the second embodiment, the outlet of the first adsorption tower 2a and the inlet of the second adsorption tower 2b are closed. As a result, the low-purity propane 100' remaining in the second adsorption towers 2b and 2b' and the third adsorption towers 2c and 2c' is stored in the temporary storage container 54 by aspirating with the compressor 65 in the same manner as in the first embodiment. On the other hand, the low-purity propane 100' remaining in the first adsorption towers 2a and 2a' is discarded by connecting the inlets 2d and 2d' of the first adsorption towers 2a and 2a' to an atmospheric pressure region. This is because the purity of the low-purity propane 100' remaining in the first adsorption towers 2a and 2a is lower than that of the low-purity propane 100' remaining in the second and third adsorption towers 2b, 2b', 2c and 2c'.

Besides, in the regeneration step of the second embodiment, the outlets of the first adsorption towers 2a and 2a' are connected to the regeneration gas supply sources 62a and 62a', and the inlets of the second adsorption towers 2b and 2b' are connected to an atmospheric pressure region. As a result, regeneration gas from the supply sources 62 and 62' is supplied to the second and third adsorption towers 2b, 2b', 2c and 2c', and regeneration gas from the regeneration gas supply sources 62a and 62a' is supplied to the first adsorption towers 2a and 2a'.

The initial adsorption step and the adsorption step of the second embodiment are carried out in the same manner as the first embodiment by connecting the outlets of the first adsorption towers 2a and 2a' to the inlets of the second adsorption towers 2b and 2b'.

According to the above-mentioned respective embodiments, water, carbon dioxide, ethane and propylene, which are impurities contained in the low-purity propane and difficult to adsorb by means of activated carbon in comparison with isobutane and normal butane, can be separated from propane by means of the zeolite molecular sieve α and the activated carbon molecular sieve β. In addition, isobutane and normal butane can be separated from the propane by means of the activated carbon γ. Moreover, oxygen and nitrogen can be separated from the propane by partial condensation in the partial condenser 3. As a result, low-purity propane can be highly purified by separating the impurities. Since the zeolite molecular sieve α and the activated carbon molecular sieve β are of type 4A, commonly used molecular sieves can be used. Furthermore, adsorption efficiency can be improved by adsorbing the impurities at a pressure that exceeds atmospheric pressure, and the adsorbents α, β and γ can be regenerated in the event that the adsorption capability is lowered.

Example 1

Low-purity propane was purified under the following conditions using the purification system 1 of the first embodiment.

The first adsorption tower 2a had a cylindrical shape having diameter of 42.6 mmφ and height of 1500 mm, and was filled with the zeolite molecular sieve α. A zeolite molecular sieve α of type 4A in the form of granules each diameter of which is 3.0 mm (MS-4A, made by Tosoh Corp.) was used for the zeolite molecular sieve α. The second adsorption tower 2b had a cylindrical shape having diameter of 95.6 mm and height of 1930 mm, and was filled with the activated carbon molecular sieve β. An activated carbon molecular sieve of type 4A type in the form of granules each diameter of which is 2.3 mm (CMS-4A-B, made by Japan EnviroChemicals Ltd.) was used for the activated carbon molecular sieve β. The third adsorption tower 2c' had a cylindrical shape having diameter of 28.4 mm and height of 1800 mm, and was filled with the activated carbon γ. Coconut shell granulated carbon having a grain size of 10 mesh through 20 mesh (Kuraray Coal GC, made by Kuraray Chemical Co.) was used for the activated carbon γ.

In the initial step, low-purity propane containing 2 ppm by volume of nitrogen, less than 0.1 ppm by volume of oxygen, 0.2 ppm by volume of carbon dioxide, 2 ppm by volume of water, 4595 ppm by volume of ethane, 2.5 ppm by volume of propylene, 484 ppm by volume of isobutane, and 15 ppm by volume of normal butane was introduced from the supply source 5 to the adsorber 2. As a result, helium filled into the adsorber 2 as the regeneration gas at atmospheric pressure prior to the initial step was replaced with the low-purity propane, and the helium concentration measured with a gas chromatography-thermal conductivity detector (GC-TCD) became 1% by volume or less. Furthermore, the adsorption pressure in the adsorption towers 2a, 2b and 2c was set to a gauge pressure of 0.50 MPa by means of the pressure regulating valve 15. The time required to accumulate pressure up to the adsorption pressure was 252 minutes.

Next, low-purity propane in a gaseous phase containing 2 ppm by volume of nitrogen, less than 0.1 ppm by volume of oxygen, 0.2 ppm by volume of carbon dioxide, 2 ppm by volume of water, 4595 ppm by volume of ethane, 2.5 ppm by volume of propylene, 484 ppm by volume of isobutane, and 15 ppm by volume of normal butane was introduced into the adsorption towers 2a, 2b and 2c and the partial condenser 3, and high-purity propane was collected in the collection container 6. At this time, the set pressure of the pressure regulating valve 23 was a gauge pressure of 0.53 MPa, the set flow rate of the flow regulator 21 was 5 L/min in the standard state, the pressure in the propane condensation region of the partial condenser 3 was a gauge pressure of 0.1 MPa, the set flow rate of the flow regulator 12 was 0.15 L/min, the temperature of each of the adsorption towers 2a, 2b and 2c was room temperature, the temperature of the constant temperature fluid circulated by the constant temperature fluid circulation device 3b was −30° C., and the purification time was 195 minutes. The acquired amount of high-purity propane in this case was 2241 g and the yield was 53.2% by weight.

A gas chromatograph-hydrogen flame ionization detector (GC-FID) for propane purity as well as the concentrations of ethane, propylene, isobutane, and normal butane, a gas chromatograph-photoionization pulsed discharge detector (GC-PDD) for oxygen, nitrogen, and carbon dioxide, and an electrostatic capacitance type dew point meter for water were used for the measurement.

When taking the points, at which the measured values of respective impurities concentration reached 1 ppm by volume, as the respective breakthrough points of the adsorbents α, β and γ for the respective impurities, the breakthrough of isobutane occurred at 190 minutes after the start of purification.

The below Table 1 indicates concentrations of impurities at the outlets of the respective adsorption towers 2a, 2b and 2c and the collection container 6 at 190 minutes after the start of purification.

According to Example 1, when the purification time was 190 minutes, it was confirmed that highly purified propane of a purity of 99.999% by volume or higher containing less than 0.1 ppm by volume of nitrogen, less than 0.1 ppm by volume of oxygen, less than 0.1 ppm by volume of carbon dioxide, less than 0.3 ppm by volume of water, 0.1 ppm by volume of ethane, less than 0.1 ppm by volume of propylene, 0.1 ppm by volume of isobutane, and less than 0.1 ppm by volume of normal butane can be obtained.

TABLE 1

| | | | | | | | | (units of concentration: ppm) |
| --- | --- | --- | --- | --- | --- | --- | --- | --- |
| | nitrogen | oxygen | carbondioxide | water | ethane | propylene | isobutane | normal butane |
| Propane supply source | 2 | <0.1 | 0.2 | 2 | 4595 | 2.5 | 484 | 15 |
| first adsorption tower outlet | 2 | <0.1 | <0.1 | <0.3 | 4597 | 2.5 | 486 | 15 |
| second adsorption tower outlet | 2 | <0.1 | <0.1 | <0.3 | <0.1 | <0.1 | 486 | 15 |
| third adsorption tower outlet | 2 | <0.1 | <0.1 | <0.3 | <0.1 | <0.1 | <0.1 | <0.1 |
| collection container | <0.1 | <0.1 | <0.1 | <0.3 | <0.1 | <0.1 | <0.1 | <0.1 |

The present invention is not limited to the above-mentioned embodiments and example. For example, since the concentrations of impurities in the low-purity propane to be purified according to the present invention has variations, the low-purity propane can contain at least one of ethane and propylene as impurity, can contain at least one of isobutane and normal butane as impurity, and can contain impurities other than nitrogen, oxygen, water, carbon dioxide, ethane, propylene, isobutane, and normal butane.

Although the first adsorption towers 2a and 2a', the second adsorption towers 2b and 2b', the third adsorption towers 2c and 2c', and the partial condenser 3 are arranged in this order from the upstream side of the propane flow path 13 in the above-mentioned embodiments, the order of the arrangement is not limited and can be changed arbitrarily. In other words, there are no limitations on the order of adsorption by means of the zeolite molecular sieve α, adsorption by means of the activated carbon molecular sieve β, adsorption by means of the activated carbon γ, and partial condensation by means of the partial condenser 3. For example, partial condensation by means of the partial condenser 3 can be carried out after adsorption by means of the zeolite molecular sieve α, and then adsorption by means of the activated carbon γ can be carried out followed by adsorption by means of the activated carbon molecular sieve β.

Although the zeolite molecular sieve α, the activated carbon molecular sieve β, and the activated carbon γ filled mutually different adsorption towers in the above-mentioned embodiments, they can fill a single adsorption tower. In this case, the zeolite molecular sieve α, the activated carbon molecular sieve β, and the activated carbon γ are layered in the single adsorption tower without mixing.

Although the propane flow path 13 in the above-mentioned embodiments has two branched flow paths 13a and 13b, there are no limitations on the number of branched flow paths, thus the first adsorption unit, the second adsorption unit, and the third adsorption unit can be connected in series in each of three or more branched flow paths.

A branched flow path is not necessary to the propane flow path, thus the first adsorption unit, the second adsorption unit, the third adsorption unit, and the partial condenser can be connected in series in a propane flow path not having a branched flow path.

Although the temporary storage step, in which the low-purity propane 100' remaining in the adsorber 2 is collected using the compressor 65 and the temporary storage container 54, is carried out after the adsorption steps in the above-mentioned embodiments, the temporary storage step, the compressor 65, and the temporary storage container 54 for the step are not necessary. Instead of the temporary storage step, low-purity propane 100' remaining in the adsorber 2 can be discarded to an atmospheric pressure region by connecting the adsorber 2 to an atmospheric pressure region after the adsorption steps. In this case, the regeneration gas is purged from inside the adsorber 2 by the low-purity propane 100' from the supply source 5 in the initial adsorption step.

EXPLANATION OF REFERENCE NUMERALS 1,1a . . . purification system, 2 . . . adsorber, 2a,2a' . . . first adsorption tower (first adsorption unit), 2b,2b' . . . second adsorption tower (second adsorption unit), 2c,2c' . . . third adsorption tower (third adsorption unit), 3 . . . partial condenser, 3b . . . constant temperature fluid circulation device (cooling means), 5 . . . low-purity propane supply source, 6 . . . high-purity propane collection container, 10 . . . exhaust path, 13 . . . propane flow path, 13a . . . first branched flow path, 13b . . . second branched flow path, 15,23 . . . pressure regulating valve (pressure regulating means), 44a,44b,44c,44a',44b',44c' . . . heater (temperature regulating means), 54 . . . temporary storage container, 55 . . . first connection switching mechanism, 62,62',62a,62a' . . . regeneration gas supply source, 65 . . . compressor, 68 . . . second connection switching mechanism

The invention claimed is:

1. A purification method for low-purity propane, comprising:
performing the following adsorption steps on the low-purity propane in any order, the low-purity propane including (i) water, (ii) carbon dioxide, (iii) ethane and/or propylene, and (iv) isobutane and/or normal butane:
adsorbing said water and carbon dioxide present in the low-purity propane in a gaseous phase by means of a zeolite molecular sieve that preferentially adsorbs water and carbon dioxide over propane;
adsorbing said ethane and/or propylene present in the low-purity propane in a gaseous phase by means of an activated carbon molecular sieve that preferentially adsorbs ethane and propylene over propane;
adsorbing said isobutane and/or normal butane present in the low-purity propane in a gaseous phase by means of activated carbon that preferentially adsorbs isobutane and normal butane over propane;
then, partially condensing propane in a state in which nitrogen and oxygen are maintained in a gaseous phase by introducing the low-purity propane in a gaseous phase into a partial condenser;
extracting nitrogen and oxygen in a gaseous phase from said partial condenser separately from the condensed propane; and
collecting high purity propane from said partial condenser into a collection container.

2. The purification method for propane according to claim 1, wherein the low-purity propane is purified to a purity of 99.995% or higher.

3. A purification system for low-purity propane comprising:
a low-purity propane supply source connected to a start of a propane flow path configured to supply a stream comprising the low-purity propane including (i) water, (ii) carbon dioxide, (iii) ethane and/or propylene, and (iv) isobutane and/or normal butane;
a first adsorption unit filled with a zeolite molecular sieve configured to preferentially adsorbs water and carbon dioxide over propane;
a second adsorption unit filled with an activated carbon molecular sieve configured to preferentially adsorbs ethane and propylene over propane;
a third adsorption unit filled with activated carbon configured to preferentially adsorbs isobutane and normal butane over propane;
a partial condenser comprising a cooling means configured to condense propane in a state in which nitrogen and oxygen are maintained in a gaseous phase;
said first adsorption unit, said second adsorption unit, said third adsorption unit, and said partial condenser are connected in series so as to form the propane flow path;
a pressure regulating means configured to regulate pressure in said propane flow path so that the low-purity propane in a gaseous phase is introduced into said first adsorption unit, said second adsorption unit, said third adsorption unit, and said partial condenser,
an exhaust path configured to extract nitrogen and oxygen in a gaseous phase from said partial condenser, and
a collection container connected to the end of said propane flow path configured to collect purified propane.

4. The purification system for low-purity propane according to claim 3, wherein said zeolite molecular sieve comprises 4A.

5. The purification system for low-purity propane according to claim 3, wherein said activated carbon molecular sieve comprises 4A.

6. The purification system for low-purity propane according to claim 5, wherein said propane flow path comprises a plurality of branched flow paths mutually connected in parallel, said first adsorption unit, said second adsorption unit, and said third adsorption unit are connected in series in each of said branched flow paths, temperature control means that regulates internal temperature in said first adsorption unit, said second adsorption unit, and said third adsorption unit is provided, a first connection switching mechanism that is capable of switching one end of each of said branched flow paths between a state of being connected to said low-purity propane supply source and a state of being connected to an atmospheric pressure region is provided, and a second connection switching mechanism that is capable of switching the other end of each of said branched flow paths between a state of being connected to said collection container, a state of being connected to a regeneration gas supply source, and a closed state is provided.

7. The propane purification system according to claim 6, wherein a compressor that has an intake port connected to the other end of each of said branched flow paths is provided, a temporary storage container that is connected to the outlet of said compressor is provided, said first switching mechanism is capable of switching one end of each of said branched flow paths between a closed state and a state of being connected to said temporary storage container, and said second switching mechanism is capable of switching the other end of each of said branched flow paths between a state of being connected to the intake port of said compressor and a state of being connected to an atmospheric pressure region.

8. The purification system according to claim 4, wherein said activated carbon molecular sieve comprises 4A.

9. The purification system according to claim 8, wherein said propane flow path comprises a plurality of branched flow paths mutually connected in parallel, said first adsorption unit, said second adsorption unit, and said third adsorption unit are connected in series in each of said branched flow paths, temperature control means that regulates internal temperature in said first adsorption unit, said second adsorption unit, and said third adsorption unit is provided, a first connection switching mechanism that is capable of switching one end of each of said branched flow paths between a state of being connected to said low-purity propane supply source and a state of being connected to an atmospheric pressure region is provided, and a second connection switching mechanism that is capable of switching the other end of each of said branched flow paths between a state of being connected to said collection container, a state of being connected to a regeneration gas supply source, and a closed state is provided.

10. The propane purification system according to claim 9, wherein a compressor that comprises an intake port connected to the other end of each of said branched flow paths is provided, a temporary storage container that is connected to the outlet of said compressor is provided, said first switching mechanism is capable of switching one end of each of said branched flow paths between a closed state and a state of being connected to said temporary storage container, and said second switching mechanism is capable of switching the other end of each of said branched flow paths between a state of being connected to the intake port of said compressor and a state of being connected to an atmospheric pressure region.

* * * * *